United States Patent
Sitte

(10) Patent No.: US 6,402,708 B1
(45) Date of Patent: Jun. 11, 2002

(54) METHOD AND APPARATUS FOR MONITORING OF CUMULATIVE-TRAUMA-SYNDROME-INDUCING ACTIVITIES

(75) Inventor: Hans Sitte, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/844,060

(22) Filed: Apr. 26, 2001

(51) Int. Cl.[7] .................................................. A61B 5/00
(52) U.S. Cl. ...................................................... 600/595
(58) Field of Search ................................. 600/546, 545, 600/587, 595

(56) References Cited

U.S. PATENT DOCUMENTS

| | | | |
|---|---|---|---|
| 5,275,174 A | * 1/1994 | Cook | 600/546 |
| 5,368,042 A | * 11/1994 | O'Neal et al. | 600/546 |
| 5,505,208 A | * 4/1996 | Toomim et al. | 600/546 |
| 5,638,831 A | 6/1997 | Brown | 128/898 |
| 5,679,004 A | * 10/1997 | McGowan et al. | 600/546 |
| 5,924,999 A | 7/1999 | Agee et al. | 600/587 |
| 5,925,007 A | 7/1999 | Ashline | 602/21 |

FOREIGN PATENT DOCUMENTS

WO    WO 00/76400 A1    12/2000

* cited by examiner

Primary Examiner—Max Hindenburg

(57) ABSTRACT

An apparatus and method for monitoring potentially-cumulative-trauma-syndrome-inducing activities by a wearer is provided. A wearable monitor and wireless transmitter are attached to a body part of the wearer. The monitor monitors activities of the body part of the wearer. The transmitter transmits signals from the monitor to a receiver. The receiver provides the transmitted signals to a processor, which analyzes the received signals and, in response to a determination that a pre-defined threshold has been exceeded, provides feedback to the wearer. The processor is connected via a local-area-network (LAN) connection to a local area-network. Ergonomics personnel can monitor the wearer and set the threshold remotely via the LAN and the LAN connection. Ergonomics personnel can also determine when the monitor is not being worn by the wearer. The monitor is adapted to resist disablement by the wearer.

22 Claims, 1 Drawing Sheet

METHOD AND APPARATUS FOR MONITORING OF CUMULATIVE-TRAUMA-SYNDROME-INDUCING ACTIVITIES

BACKGROUND

1. Technical Field of the Invention

The present invention relates in general to the field of biofeedback systems, and in particular, by way of example but not limitation, to monitoring of potentially cumulative-trauma-syndrome-inducing activities.

2. Description of Related Art

Many people suffer from repetitive-stress injuries, also known as cumulative-trauma syndrome (CTS). Carpal tunnel syndrome is an example of a CTS. CTS also includes tendonitis, cysts, and bursitis. CTS is one of the most common occupational health hazards in industrialized countries today. Numbness, tingling, burning and throbbing, weakness, and even paralysis of fingers, hands, and arms are typical symptoms of CTS. People who suffer from CTS often require surgery, lose time and productivity at work, and, in extreme cases, become unemployed. In some cases, sufferers from CTS cannot perform simple tasks such as picking up a tennis ball. Even if such a simple task can be performed by a person with CTS, it is often excruciatingly painful.

Biofeedback can be an important tool for helping those susceptible to CTS. However, it is an effective tool only if it can be employed in a way that allows a susceptible person to avoid behaviors that might lead CTS. Oftentimes, a person will develop CTS after performing a given motion an excessive number of times and/or in a less-than-biomechanically-ideal fashion without knowing that their behavior is contributing to or even causing CTS. Once the person has developed CTS, cessation of the activities that led to its development are often not effective in reversing the condition. In the case of CTS, the axiom that "an ounce of prevention is worth a pound of cure" undoubtedly applies.

Many attempts have been made to ameliorate the effects of and appropriately treat CTS once it has manifested itself. Other methods have been described that attempt to work around limitations imposed by CTS. However, these methods do not allow people who are susceptible to CTS to avoid developing it in the first place. There is accordingly a need for a method and apparatus for monitoring of potentially-cumulative-trauma-syndrome-inducing activities that solves these and other drawbacks.

SUMMARY

These and other deficiencies are overcome by the present invention. In a first embodiment of the present invention, an apparatus for monitoring potentially-cumulative-trauma-syndrome-inducing activities includes a wearable muscular-tension monitor, a wearable wireless transmitter, a receiver, and a processor. The monitor is adapted to be worn substantially on a body part of a wearer. The transmitter is interoperably connected to the monitor and is adapted to transmit signals generated by the monitor. The transmitter transmits only when the transmitter is within a pre-defined distance from the receiver. The processor is interoperably connected to the receiver. The processor is adapted to analyze the received signals, determine whether a pre-determined muscular-tension threshold has been exceeded by the wearer, and provide feedback to the wearer in response to a determination that the threshold has been exceeded.

In another embodiment of the present invention, a method of monitoring potentially-cumulative-trauma-syndrome-inducing activities includes monitoring, via a wearable monitor, muscular tension of a body part of a wearer. In response to the step of monitoring, a plurality of signals are generated. The plurality of signals are wirelessly transmitted via a wearable transmitter. A receiver located within a pre-determined distance from the transmitter receives the transmitted signals. The received signals are analyzed. Based on the analyzed signals, a determination is made whether a pre-determined muscular-tension threshold has been exceeded by the wearer. Feedback is provided to the wearer in response to a determination that the threshold has been exceeded.

The above-described and other features of the present invention are explained in detail below with reference to illustrative examples shown in the accompanying Drawings. Those of ordinary skill in the art will appreciate that the described embodiments are provided for purposes of illustration and understanding and that numerous equivalent embodiments are also contemplated in this patent application.

BRIEF DESCRIPTION OF THE DRAWINGS

A more complete understanding of embodiments of the present invention can be achieved by reference to the following Detailed Description when taken in conjunction with the accompanying Drawings wherein.

DETAILED DESCRIPTION OF THE PREFERRED EXEMPLARY EMBODIMENTS OF THE PRESENT INVENTION

In the following Description, for purposes of explanation and not limitation, specific details are set forth in order to provide a thorough understanding of embodiments of the present invention. However, it will be apparent to those of ordinary skill in the art that the present invention can be practiced in other embodiments that depart from these specific details. In other instances, detailed descriptions of well-known methods, devices, logical code (e.g., hardware, software, firmware), and the like are omitted so as not to obscure description of embodiments of the present invention with unnecessary detail. Preferred embodiments of the present invention and its advantages are best understood by referring to FIGS. 1–2 of the Drawings.

Figure 1:
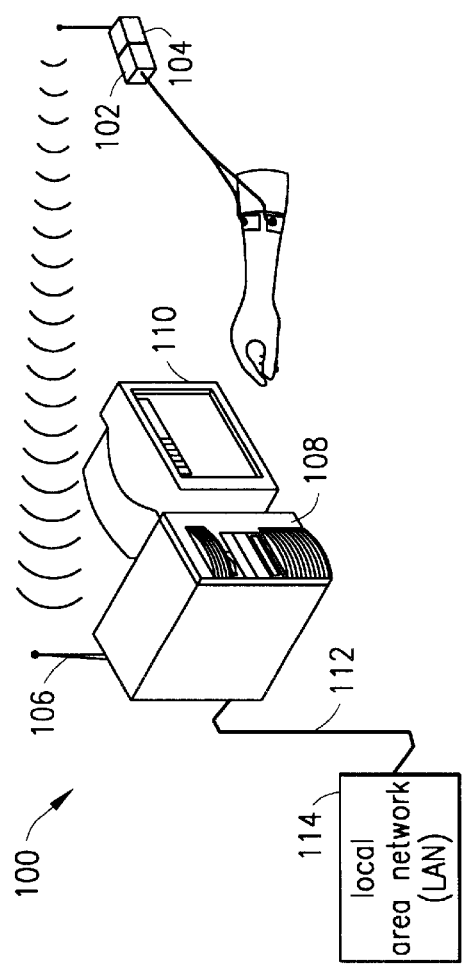
FIG. 1 is a diagram illustrating an apparatus for monitoring potentially-cumulative-trauma-syndrome-inducing activities in accordance with the present invention.

FIG. 1 is a diagram illustrating an apparatus 100 for monitoring potentially-cumulative-trauma-syndrome-inducing activities in accordance with the present invention. The exemplary apparatus 100 includes a wearable muscular-tension monitor 102, a transmitter 104, a receiver 106, a processor 108, a display 110, a local area network (LAN) connection 112, and a LAN 114. The monitor 102 and the transmitter 104 preferably are combined into a integral unit that can be easily worn by a wearer during his or her normal working activities. The monitor 102 and the transmitter 104 are shown attached to an arm of a human being, although the monitor 102 and the transmitter 104 can be attached to other body parts of human beings or animals such as, for example, the back, neck or wrist of a human being. Although in the embodiment shown, the monitor 102 and the transmitter 104 form an integral unit, other embodiments of the combined monitor 102 and transmitter 104 could include, for example, a wearable monitor that is interoperably connected by wires to a transmitter that could be carried in a pocket of clothing while the monitor 102 is attached to an arm of the wearer.

In a preferred embodiment, the transmitter 104 is sufficiently small and lightweight to be wearable during normal activities of the wearer. The monitor 102 and the transmitter 104 are preferably battery-powered and/or rechargeable, so that the wearer can move about freely while only the monitor 102 and the transmitter 104 are connected to or worn by the wearer. In a preferred embodiment, the monitor 102 generates electrical signals usually expressed in microvolts, that result from muscular activity of the body part to which the monitor 102 is attached. These signals are converted to radio signals and are transmitted wirelessly by the transmitter 104 to the receiver 106. In a preferred embodiment, the transmitter 104 transmits only when the transmitter 104 is within a predefined distance from the receiver 106. The signals can be transmitted according to any acceptable wireless format including, but not limited to, optical, acoustic, and electromagnetic formats.

Upon receipt of the transmitted signals, the receiver 106, which is interoperably connected to the processor 108, provides the received signals to the processor 108. Although depicted as a personal-computer-type device, the processor 108 can be virtually any processor-based device or web appliance adapted for the needs of the embodiments of the present invention. The processor 108 analyzes the received signals, determines whether a predetermined muscular-tension threshold has been exceeded by the wearer, and provides feedback to the wearer responsive to a determination by the processor 108 that the threshold has been exceeded. In a preferred embodiment, the transmitter 104 and the receiver 106 operate as an ad-hoc wireless system, such as, for example a system operating according to BLUETOOTH™. The receiver 106 and the transmitter 104 are also adapted in a preferred embodiment to communicate only with one another, so that, in the event the wearer moves into an area covered by a different receiver than the receiver 106, communication between the transmitter 104 and the different receiver will not occur. In a preferred embodiment, the processor 108 is interoperably connected to the LAN 114 by the LAN connection 112. Connection of the processor 108 to the LAN 114 permits ergonomics personnel to monitor activities of the wearer detected by the monitor 102 and also to set the pre-determined threshold for the wearer. A LAN system is not the sole technique for communicating the monitored activities to ergonomics personnel. For example, telephone, internet, hardwired, and wireless technologies can also be utilized by embodiments of the present invention.

In the event that the pre-determined threshold is exceeded, the processor 106 provides feedback to the wearer. This feedback can be, for example, display of a message on the display 110, playing an audible signal, or the like. The feedback can, for example, instruct the wearer to take a break, stop work, move to a different task, perform the task in a different manner, or the like.

It has been found that, in some instances, muscular-tension monitors, such as, for example, the Pocket Ergometer sold by Biomechanics Corporation of America, can easily be disabled by a wearer. The Pocket Ergometer provides an audible feedback to the wearer based upon muscular-tension thresholds. The wearer can turn off the Pocket Ergometer simply by pressing a button. In contrast, a preferred embodiment of the present invention resists disablement by the wearer, by, for example, being formed into a structure that cannot be opened by the wearer without special tools and which has no wearer-accessible on/off switch. In addition, in a preferred embodiment, the monitor is adapted to detect when it is not being worn by the wearer, so that, for example, ergonomics personnel can notify the wearer to put the monitor back on if it has been removed.

The apparatus 100 can therefore be used to provide virtually-instantaneous feedback to a wearer regarding activities of the wearer that cause muscular-tension levels in a monitored body part to exceed a muscular-tension threshold. The threshold is preferably set remotely by ergonomics personnel. When the threshold has been exceeded, feedback is provided to the wearer in order to cause the wearer's muscular tension to be reduced in order to attempt to prevent the onset of cumulative-trauma syndrome.

Figure 2:
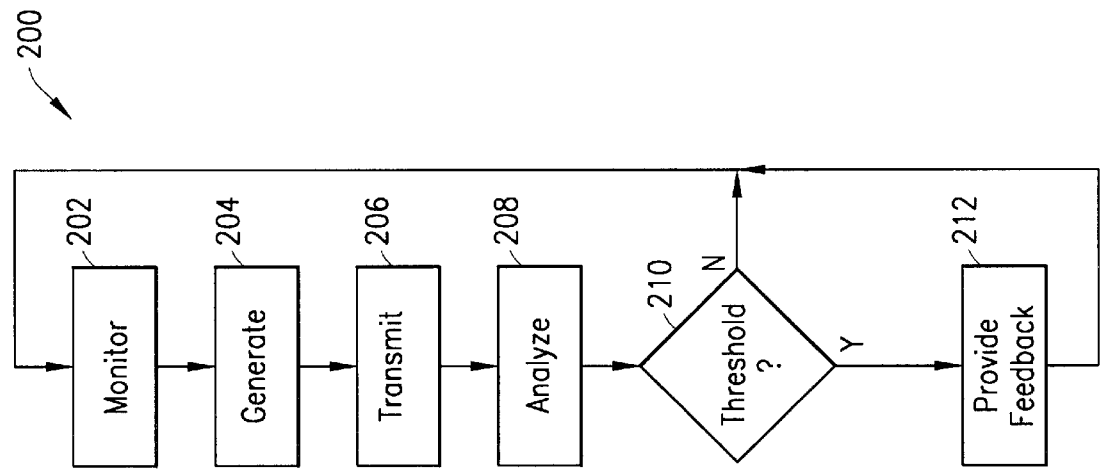
FIG. 2 is a flow chart that illustrates exemplary operation of the apparatus FIG. 1 in accordance with the present invention.

FIG. 2 is a flow chart that illustrates an exemplary operation of the apparatus 100 in accordance with the present invention. A flow 200 begins at step 202, wherein muscular-tension levels of the body part of the wearer are monitored. At step 204, signals representing the muscular-tension level are generated by a monitoring device. At step 206, the signals generated by the monitoring device at step 204 are transmitted wirelessly by the transmitter 104 to the receiver 106.

Because the receiver 106 is interoperably connected to the processor 108, the processor 108 is able, at step 208, to analyze the signals received by the receiver 106. At step 210, a determination is made whether a predetermined threshold relative to the wearer has been exceeded. If it is so determined, execution proceeds to step 212. At step 212, feedback is provided to the wearer. If, at step 210, it is not determined that a threshold has been exceeded, execution moves to step 202.

FIG. 2 illustrates that a body part of a wearer is monitored and, from the monitoring, signals are generated which are transmitted to a receiver. Upon receipt of the signals, the signals are analyzed by a processor, which determines whether a threshold has been exceeded. If so determined, feedback is provided to the wearer. An object of the feedback is to cause the wearer to change behavior in order to prevent the onset of cumulative-trauma syndrome.

Although preferred embodiment(s) of the present invention have been illustrated in the accompanying Drawings and described in the foregoing Description, it will be understood that the present invention is not limited to the embodiment(s) disclosed, but is capable of numerous rearrangements, modifications, and substitutions without departing from the spirit and scope of the present invention as set forth and defined by the following claims.

What is claimed is:

1. An apparatus for monitoring potentially-cumulative-trauma-syndrome-inducing activities comprising:
 a wearable muscular-tension monitor adapted to be worn substantially on a body part of a wearer;
 a wearable wireless transmitter interoperably connected to the monitor wherein the transmitter is adapted to transmit signals generated by the monitor;
 a receiver adapted to receive the transmitted signals, wherein the transmitter transmits only when the transmitter is within a pre-defined distance from the receiver; and
 a processor electrically connected to the receiver, wherein the processor is adapted to:
 analyze the received signals;
 determine whether a predetermined cumulative muscular-tension threshold has been exceeded by the wearer; and provide feedback to the wearer responsive to a determination that the cumulative muscular-tension threshold has been exceeded.

2. The apparatus of claim 1, wherein the receiver is adapted to receive signals from only the transmitter.

3. The apparatus of claim 2, wherein the transmitter and the monitor comprise an integral unit.

4. The apparatus of claim 1, wherein the processor is accessible to a location that is distal from said processor such that ergonomics personnel can set said predetermined cumulative muscular-tension threshold from said distal location.

5. The apparatus of claim 3, wherein the integral unit is battery-powered.

6. The apparatus of claim 4, further comprising a network interoperably connected to the processor, wherein the network permits the ergonomics personnel to remotely set the threshold from said distal location.

7. The apparatus of claim 1, wherein the feedback is provided via a visual display.

8. The apparatus of claim 1, wherein the body part is a wrist of a human being.

9. The apparatus of claim 1, wherein the body part is a back of a human being.

10. The apparatus of claim 4, wherein the monitor and transmitter are adapted to resist disablement by the wearer.

11. The apparatus of claim 1, wherein the monitor is adapted to detect when it is not being worn and is adapted to provide a signal for informing ergonimics personnel the apparatus is not being worn.

12. A method of monitoring potentially-cumulative-trauma-syndrome-inducing activities comprising the steps of:

monitoring, via a wearable monitor, muscular tension of a body part of a wearer;

generating a plurality of signals responsive to the step of monitoring;

wirelessly transmitting, via a wearable transmitter, the plurality of signals;

receiving, by a receiver located within a pre-determined distance from the transmitter, the transmitted signals;

analyzing the received signals;

determining, based on the analyzed signals, whether a pre-determined muscular-tension threshold has been exceeded by the wearer; and providing feedback to the wearer responsive to a determination that the threshold has been exceeded.

13. The method of claim 12, wherein the receiver only receives signals from the transmitter.

14. The method of claim 12, wherein the transmitter and the monitor comprise an integral unit.

15. The method of claim 12, further comprising the step of setting, prior to the step of monitoring, by ergonomics personnel, the pre-determined threshold for the wearer.

16. The method of claim 12, wherein the unit is battery-powered.

17. The method of claim 12, wherein the threshold is set via a local area network interoperably connected to the processor.

18. The method of claim 12, wherein the step of providing feedback is performed via a display associated with the processor.

19. The method of claim 12, wherein the body part is a wrist of a human being.

20. The method of claim 12, wherein the body part is a back of a human being.

21. The method of claim 12, wherein the monitor and transmitter are adapted to resist disablement by the wearer.

22. The method of claim 12, wherein the monitor is adapted to detect when the wearer is not wearing the monitor.

\* \* \* \* \*